Figure 1:
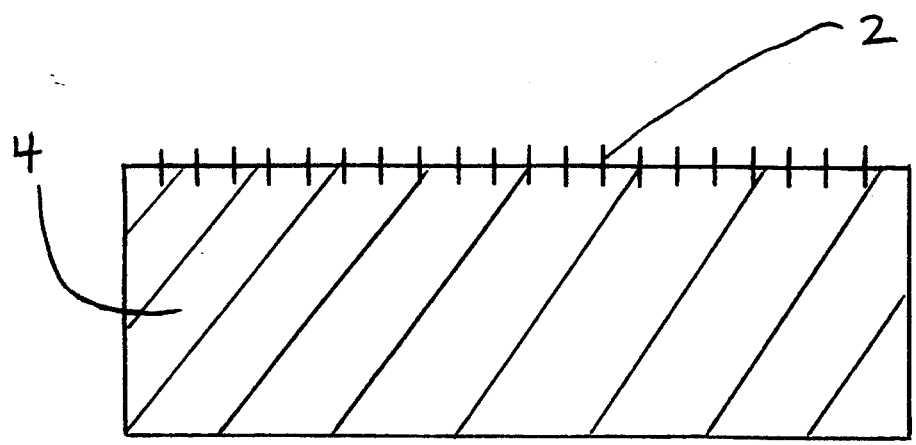

United States Patent [19]
Bulan et al.

[11] Patent Number: 5,364,507
[45] Date of Patent: Nov. 15, 1994

[54] PROCESS FOR THE PRODUCTION OF PERFLUOROALKYLSULPHONYL FLUORIDES AND ELECTRODES FOR PERFORMANCE OF THE PROCESS

[75] Inventors: Andreas Bulan, Langenfeld; Rainer Weber, Odenthal; Zbigniew Muziol, Cologne; Hartmut Schlecker; Hans-Heinrich Moretto, both of Leverkusen, all of Germany

[73] Assignee: Bayer AG, Leverkusen, Germany

[21] Appl. No.: 100,241

[22] Filed: Aug. 2, 1993

[30] Foreign Application Priority Data

Aug. 13, 1992 [DE] Germany ............................ 4226758

[51] Int. Cl.$^5$ ............................................. C25B 3/08
[52] U.S. Cl. .................................................. 204/59 F
[58] Field of Search ............... 204/59 F, 292, 290 R; 252/513; C25B 3/08, 11/06

[56] References Cited

U.S. PATENT DOCUMENTS 3,919,057 11/1975 Plattner et al. ............... 204/59 F
3,980,534 9/1976 Drakesmith ................ 204/59 F

FOREIGN PATENT DOCUMENTS 0451589 10/1991 European Pat. Off. .
2243274 4/1975 France .
2442106 3/1975 Germany .

OTHER PUBLICATIONS

Enno Hollitzer and Peter Sartori, "Die elektrochemische Fluorierung—ein Überlick" (Chem-Ing.-Tech. 58) (1986) No. 1, S. 31–38.
Eugen G. Leuze, *Schriftenreihe Galvanotechnik*. "Die galvanische Vericklung", (1984) no month available.
Abstract of J62060885-A MITV (Sep. 11, 1985); Mitsubishi Metal KK.
Orbit Abstract of FR-A 2 243 274 no date available.
Orbit Abstract of EP-A 0 451 589 no date available.

*Primary Examiner*—Kathryn Gorgos
*Attorney, Agent, or Firm*—Connolly & Hutz

[57] ABSTRACT

The present invention provides a process for the production of perfluoroalkylsulphonyl fluorides of the formula $C_nF_{2n+1}SO_2F$ with $n=6-10$ by electrochemical fluorination of alkylsulphonyl halides of the general formula $C_nH_{2n+1}SO_2X$ with $n=6-10$ and $X=F$, Cl, Br or I in hydrogen fluoride, which process is characterised in that electrodes are used which consist of nickel with a columnar structure or which are coated with nickel with a columnar structure as shown in FIG. 1.

The invention also provides electrodes for the production of perfluoroalkylsulphonyl fluorides from the corresponding alkylsulphonyl halides by electrochemical fluorination in hydrogen fluoride, which electrodes are characterised in that they consist of nickel with a columnar structure or are coated with nickel with a columnar structure.

9 Claims, 1 Drawing Sheet

PROCESS FOR THE PRODUCTION OF PERFLUOROALKYLSULPHONYL FLUORIDES AND ELECTRODES FOR PERFORMANCE OF THE PROCESS

BACKGROUND OF THE INVENTION

1. Field of the Invention

The invention relates to a process for the production of perfluoroalkylsulphonyl fluorides by electrochemical fluorination of the corresponding alkylsulphonyl halides and to electrodes for the performance of the process.

2. Description of the Prior Art

The production of fluorinated compounds by electrochemical fluorination proceeds according to E. Hollitzer and P. Satori, *Chem.-Ing.-Tech.* 58 (1986), no. 1, 31–38 by anodic oxidation in a solvent containing fluoride. Anode materials used in the process are nickel, carbon and platinum. If hydrogen fluoride is used as the solvent, nickel anodes are preferably used. Perfluorinated compounds are obtained from the process.

If alkylsulphonyl halides of the formula $C_nH_{2n+1}SO_2X$ with n=6–10 and X=F, Cl, Br, I are electrochemically fluorinated in hydrogen fluoride on nickel electrodes, perfluoroalkylsulphonyl fluorides, $C_nF_{2n+1}SO_2F$, are produced. A disadvantage of this process for the production of perfluoroalkylsulphonyl fluorides is considerable anode corrosion. This corrosion gives rise to problems from nickel corrosion products when operating the electrolysis cells, which corrosion products clog the electrode interstices and block valves and pipework. For this reason, prolonged, continuous electrochemical fluorination is not possible, which greatly diminishes the economic viability of the process.

The object of the invention was, therefore, to provide a process for the production of perfluoroalkylsulphonyl fluorides by electrochemical fluorination in which the stated disadvantages do not arise.

It was surprisingly found that the stated disadvantages do not arise if the anodes consist of nickel with a columnar structure or are coated with nickel with such a structure.

DESCRIPTION OF THE INVENTION AND PREFERRED EMBODIMENTS

The present invention provides a process for the production of perfluoroalkylsulphonyl fluorides of the formula $C_nF_{2n+1}SO_2F$ with n=6–10 by electrochemical fluorination of alkylsulphonyl halides of the general formula $C_nH_{2n+1}SO_2X$ with n=6–10 and X=F, Cl, Br or I in hydrogen fluoride, which process is characterised in that electrodes are used which consist of nickel with a columnar structure or which are coated with nickel with a columnar structure.

FIG. 1 is a cross-sectional view of a portion of an electrode of the present invention which consists of a base material 4 and a columnar nickel layer 2 located on the surface of the base material.

In electrodes which are coated with columnar nickel, another metal apart from nickel, such as for example iron or copper, may also be used as the electrode material, Nickel with a columnar structure is obtained, for example, by electrolytic deposition of nickel onto a base material (*Praktische Galvanotechnik, Ein Lehr- und Handbuch*, 4th edition 1984, Eugen G Leuze Verlag, Saulgau).

Preferably, in the process according to the invention, octylsulphonyl halides of the formula $C_8H_{17}SO_2X$ with X=F, Cl or Br are electrochemically fluorinated to perfluorooctylsulphonyl fluoride.

The invention also provides electrodes for the production of perfluoroalkylsulphonyl fluorides from the corresponding alkylsulphonyl halides by electrochemical fluorination in hydrogen fluoride, which electrodes are characterised in that they consist of nickel with a columnar structure or are coated with nickel with a columnar structure.

If, in the production of perfluoroalkylsulphonyl fluorides of the formula $C_nF_{2n+1}SO_2F$ with n=6–10, anodes made of nickel with a columnar structure or anodes which are coated with nickel with a columnar structure are used, no corrosion is observed. The electrochemical fluorination may thus be operated continuously for prolonged periods. Downtime periods during which electrode bundles have to be changed because they are clogged with nickel corrosion products are not required. Moreover, the longer operating life of the anodes improves the economic viability of the process.

The electrochemical fluorination is customarily performed under the following conditions.

The electrolysis cells used for the electrochemical fluorination consist of nickel or another material which is resistant to corrosion by hydrogen fluoride, such as for example perfluorinated plastics. The cathodes consist of nickel or iron. The electrodes according to the invention are used as anodes. The distances between the electrodes are normally 2 to 5 mm. The electrolyte temperature is customarily between 0° C. and 20° C. It may, however, also be between 20° C. and 50° C., as described in DE-A 2 442 106. Comprehensive details relating to the structure and operating conditions of electrolysis cells are to be found in the literature.

Hydrogen fluoride and the alkylsulphonyl halide to be fluorinated are placed in an electrolysis cell. Thereupon, a constant cell voltage of 4 to 6 V is applied and the compound to be fluorinated is continuously or intermittently added on the basis of the quantity of electricity passed and the given stoichiometry (see general reaction equation):

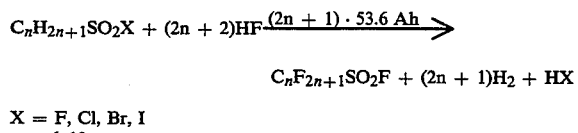

$$C_nH_{2n+1}SO_2X + (2n + 2)HF \xrightarrow{(2n + 1) \cdot 53.6 \text{ Ah}}$$

$$C_nF_{2n+1}SO_2F + (2n + 1)H_2 + HX$$

X = F, Cl, Br, I
n = 6–10

Hydrogen fluoride is added as it is consumed. The fluorinated product is periodically removed from the cell at specified intervals of time.

The invention is more closely illustrated by means of the following examples.

EXAMPLE 1 (prior art)

Electrochemical fluorination of octylsulphonyl fluoride on sheet nickel electrodes with a polycrystalline structure.

Perfluorooctylsulphonyl fluoride ($C_8F_{17}SO_2F$) is produced by the electrochemical fluorination of octylsulphonyl fluoride ($C_8H_{17}SO_2F$). To this end, the electrolysis cell is filled with 26.5 kg of hydrogen fluoride. The electrolyte temperature is 10° C. The octylsulphonyl fluoride is continuously added according to the given stoichiometry.

The anodes and cathodes consist of polycrystalline nickel sheet (2 mm thick). The dimensions of an anode are 25 cm in width and 20 cm in height. The anode surface area is 9750 cm$^2$.

At a voltage of on average 5 V, 3.1 kg of octylsulphonyl fluoride are reacted with a charge of 15,142 Ah over 1532 operating hours. The loss of nickel during the test period is 499 g; this corresponds to 32.9 mg per Ampere-hour.

EXAMPLE 2 (prior art)

Electrochemical fluorination on polycrystalline nickel foam

Perfluorooctylsulphonyl fluoride ($C_8F_{17}SO_2F$) is produced by electrochemical fluorination of octylsulphonyl fluoride ($C_8H_{17}SO_2F$). To this end, the electrolysis cell is filled with 650 g of hydrogen fluoride. The electrolyte temperature is 15° C. The octylsulphonyl fluoride is added according to the given stoichiometry.

The anodes consist of polycrystalline nickel foam from the company NiTech, Fontenay-sous-Bois Cédex, France (type MN 045 0200 050), and the cathodes of polycrystalline nickel sheet. The dimensions of an anode are: 7 cm high, 5 cm wide, 0.2 cm thick. The total geometric anode surface area is 271 cm$^2$.

At a voltage of on average 5 V, an attempt is made to react 20 g of octylsulphonyl fluoride. After 191 h and 84.7 Ah the anodes are so heavily corroded that the test has to be halted as the electrodes have partially dissolved.

The loss of nickel during the test period is 3.5 g, this corresponds to 41.3 mg of nickel per Ampere-hour.

EXAMPLE 3 (according to the invention)

Electrochemical fluorination on columnar nickel.

Perfluorooctylsulphonyl fluoride ($C_8F_{17}SO_2F$) is produced by electrochemical fluorination of octyl sulphonyl fluoride ($C_8F_{17}SO_2F$). To this end, the electrolysis cell is filled with 27 kg of hydrogen fluoride. The electrolyte temperature is 10° C. The octylsulphonyl fluoride is added according to the given stoichiometry.

The anodes consist of nickel foam from the company Dunlop, Coventry, Great Britain (Retimet), wherein the nickel has a columnar structure. The dimensions of an anode are: 20 cm×25 cm×1 cm. The electrode stack consists of 7 anodes and 8 cathodes. The total geometric anode surface area is 6,825 cm$^2$.

At a voltage of on average 5 V, 106.1 kg of octylsulphonyl fluoride are reacted with 493,326 Ah over 19,782 hours. No electrode corrosion is detectable on completion of the test.

What is claimed is:

1. Process for the production of perfluoroalkylsulphonyl fluorides of the formula $C_nF_{2n+1}SO_2F$ with n=6−10 by electrochemical fluorination of alkylsulphonyl halides of the formula $C_nH_{2n+1}SO_2X$ with n=6−10 and with X=F, Cl, Br or I in hydrogen fluoride, wherein electrodes are used which consist of nickel with a columnar structure or which are coated with nickel with a columnar structure.

2. Process according to claim 1, wherein octylsulphonyl halides of the formula $C_8H_{17}SO_2X$ with X=F, Cl or Br are electrochemically fluorinated to perfluorooctylsulphonyl fluoride in hydrogen fluoride.

3. Process according to claim 2, wherein said electrodes consist essentially of iron or copper which is coated with nickel with a columnar structure.

4. Process according to claim 2, wherein said electrochemical fluorination takes place at a temperature of from about 0° to 50° C.

5. Process according to claim 2, wherein said electrochemical fluorination takes place at a temperature of from about 0° to 20° C.

6. Process according to claim 1, wherein said electrodes consist essentially of iron or copper which is coated with nickel with a columnar structure.

7. Process according to claim 1, wherein said electrochemical fluorination takes place at a temperature of from about 0° to 50° C.

8. Process according to claim 1, wherein said electrochemical fluorination takes place at a temperature of from about 0° to 20° C.

9. Electrodes for the production of perfluoroalkylsulphonyl fluorides from the corresponding alkylsulphonyl halides by electrochemical fluorination in hydrogen fluoride, wherein the electrodes consist of nickel with a columnar structure or are coated with nickel with a columnar structure.

* * * * *

UNITED STATES PATENT AND TRADEMARK OFFICE
CERTIFICATE OF CORRECTION

PATENT NO. : 5,364,507
DATED : November 15, 1994
INVENTOR(S) :
    Bulan et al.

It is certified that error appears in the above-indentified patent and that said Letters Patent is hereby corrected as shown below:

Column 4, line 12, the words "the formula $C_nH_{2+1}SO_2X$" should read -- the formula $C_nH_{2n+1}SO_2X$ --.

Signed and Sealed this

Twenty-ninth Day of August, 1995

Attest:

BRUCE LEHMAN

*Attesting Officer*      *Commissioner of Patents and Trademarks*